(12) United States Patent
Tchoreloff et al.

(10) Patent No.: US 8,029,825 B2
(45) Date of Patent: Oct. 4, 2011

(54) LOW-DOSE TABLETS HAVING A NETWORK OF POLYMERS

(75) Inventors: Pierre Tchoreloff, Bures sur Yvette (FR); Bernard Leclerc, Igny (FR); Guillaume Benoist, Chartres (FR); Laurent Bertocchi, Syvains les Moulins (FR)

(73) Assignee: Ethypharm, Houdan (FR)

( * ) Notice: Subject to any disclaimer, the term of this patent is extended or adjusted under 35 U.S.C. 154(b) by 816 days.

(21) Appl. No.: 10/579,045

(22) PCT Filed: Nov. 10, 2004

(86) PCT No.: PCT/FR2004/002890
§ 371 (c)(1),
(2), (4) Date: Aug. 16, 2007

(87) PCT Pub. No.: WO2005/046647
PCT Pub. Date: May 26, 2005

(65) Prior Publication Data
US 2008/0031946 A1  Feb. 7, 2008

(30) Foreign Application Priority Data
Nov. 10, 2003  (FR) ...................................... 03 13188

(51) Int. Cl.
*A61K 9/22* (2006.01)
(52) U.S. Cl. ......................... 424/489; 424/488; 424/479
(58) Field of Classification Search ........................ None
See application file for complete search history.

(56) References Cited

U.S. PATENT DOCUMENTS

| 5,292,534 | A | * | 3/1994 | Valentine et al. ............. 424/451 |
| 5,464,632 | A | | 11/1995 | Cousin et al. |
| 5,607,697 | A | | 3/1997 | Alkire et al. |
| 5,783,215 | A | * | 7/1998 | Arwidsson et al. ........... 424/501 |
| 5,855,914 | A | * | 1/1999 | Koyama et al. ............... 424/494 |
| 6,077,533 | A | | 6/2000 | Oshlack et al. |
| 6,077,544 | A | | 6/2000 | Debregeas et al. |
| 6,156,911 | A | * | 12/2000 | Doswald et al. ............. 549/328 |
| 6,416,786 | B1 | | 7/2002 | Mulye et al. |
| 6,607,751 | B1 | * | 8/2003 | Odidi et al. ................... 424/488 |
| 6,656,503 | B1 | * | 12/2003 | Sherman ........................ 424/474 |
| 6,780,436 | B1 | | 8/2004 | Lopez-Cabrera et al. |
| 7,157,102 | B1 | * | 1/2007 | Nuwayser ..................... 424/490 |
| 2003/0017210 | A1 | | 1/2003 | Debregeas et al. |
| 2004/0242640 | A1 | * | 12/2004 | Desai et al. ................... 514/332 |
| 2005/0152976 | A1 | | 7/2005 | Chenevier et al. |
| 2006/0257482 | A1 | * | 11/2006 | Kumar et al. ................. 424/469 |

FOREIGN PATENT DOCUMENTS

| EP | 0 361 874 A2 | 4/1990 |
| EP | 0 548 356 B1 | 6/1993 |
| EP | 1 032 374 B1 | 9/2000 |
| JP | 68-109414 | 6/1983 |
| JP | 01-091757 | 4/1989 |
| JP | 2001-199878 | 7/2001 |
| JP | 2002-516166 | 6/2002 |
| JP | 2003-518062 | 6/2003 |
| WO | WO 99/61006 | 12/1999 |
| WO | WO 01/45706 A1 | 6/2001 |
| WO | WO 03/090724 A1 | 11/2003 |

OTHER PUBLICATIONS

Damian et al, 2000. Physicochemical characterization of solid dispersions of the antiviral agent UC-781 with polyethylene glycol 6000 and Gelucire 44/14.; European Journal of Pharmaceutical Sciences, vol. 10:311-322.*
Trinidade and Grosso, 2000. The stability of ascorbic acid microencapsuled in gransules of rice starch and gum arabic. J. Microencapsulation, vol. 17(2):169-176.*
Gennaro 1990. Remington's Pharmaceutical Sciences. Chapter 89. Oral Solid Dosage Forms. pp. 1633-1665.*
English-language translation of Rejection of Japanese Patent Application No. 2006-538898, Apr. 23, 2010.

* cited by examiner

*Primary Examiner* — Robert A Wax
(74) *Attorney, Agent, or Firm* — Buchanan Ingersoll & Rooney PC

(57) ABSTRACT

The invention relates to low-dose tablets obtained by directly compressing microgranules essentially constituted of a neutral support covered by a polymeric layer containing at least one pharmaceutically acceptable polymer and permitting the modified release of active substances in an aqueous medium, to which an active layer containing at least one active substance is applied. The inventive tablets advantageously exhibit a matrix effect similar to that obtained with conventional matrix tablets that depends on the nature of the polymer(s) used for the constitution of the polymeric layer. This matrix effect makes it possible to modify the release profile of the transported active substance based on the type of the polymer used. These tablets are particularly suited for realizing low-dose tablets. The invention also relates to a method for producing these tablets and to the use thereof, particularly for administering active substances in low to very low doses.

45 Claims, 5 Drawing Sheets

Before compression: granular stacking of the applied granules

No continuous polymer network

Discontinuous network

Continuous network
Composition percolation

After compression: within the tablets

No continuous polymer network
No percolation

Thin continuous network
Percolation

Thick continuous network
Percolation

LOW-DOSE TABLETS HAVING A NETWORK OF POLYMERS

CROSS-REFERENCE TO RELATED APPLICATIONS

This application is the United States national phase of International Application No. PCT/FR2004/0002890, filed Nov. 10, 2004, which claims the priority of Application No. 03/13188, filed in France on Nov. 10, 2003, said applications being expressly incorporated by reference herein in their entireties and relied upon.

The present invention relates to tablets administrable by oral route, intended for the delivery of active principles, and in particular of low-dose active principles, allowing a modified release of these active principles.

The tablets according to the invention are obtained by direct compression of microgranules comprised of a neutral support to which is applied a polymeric layer, to which is applied an active layer containing at least one active principle.

Thus, the active principle is located in the active layer but not in the polymeric layer, and this polymeric layer is inserted between the neutral support and the active layer.

The present invention also relates to the method for obtaining the aforesaid tablets, as well as to the use thereof for the administration by oral route of medicaments, in particular of low-dose medicaments.

Neutral Support

By a "neutral support," a "neutral core" or more simply a "neutral" is meant a spherical or quasi-spherical inert support of a size between 50 µm and 3 mm, preferentially between 100 µm and 1000 µm, such as those commonly used in the pharmaceutical industry as a support base for active principles, for example for the constitution of microgranules.

In the present invention, microspheres comprised of sucrose and of corn starch will be used preferentially as the neutral support. These microspheres, which are used routinely in the pharmaceutical industry, are defined in the European Pharmacopeia under the term "sugar spheres," and respond in particular to the following specifications: not to contain more than 92% by dry weight of sucrose, with the remaining weight consisting of corn starch.

Direct Compression

The term "direct compression" is used to describe the step of a method for obtaining tablets consisting of compressing the mixture of excipients "directly," that is, without having to subject said mixture to a transformation before compression, a transformation such as granulation, for example.

Such a method of direct compression is possible only if the mixture to be compressed exhibits suitable qualities in terms of granulometry, of packing and of flow, and exhibits suitable mechanical properties. When this step of direct compression is not possible for the reasons cited above, a preliminary step must be called upon, for example a granulation step, which modifies the texture of the granular system and therefore the granulometry and the compression behavior of the mixture to be compressed.

The direct compression step can comprise the addition of certain excipients supporting the compression step such as certain conventional lubricants, for example.

Functionalized Microgranules and Excipients

The microgranules of the present invention refer to spherical pharmaceutical dosage units, comprised in their center of a neutral support, coated with at least one polymeric layer which itself is coated with at least one layer containing the active principle. Such microgranules are assembled in tablets by direct compression in accordance with the present invention.

The term "functionalized excipient" is used to indicate the neutral support coated with the polymeric layer after drying. Indeed, this specific association corresponds to a functionalization of the excipients on which the active layer will be deposited, which makes these excipients favorable for obtaining a system with modified release after compression, in accordance with the invention.

Low-Dose Tablets

In the present application, by "low-dose tablets" is meant tablets whose load in active principle is low to very low, that is, lower than 50 mg per tablet, preferentially lower than 25 mg per tablet, preferentially still lower than 10 mg per tablet. In particular, the tablets in conformity with the present invention are suitable for formulations whose dosages can be on the order of a microgram, insofar as the method of preparation of these tablets describes below makes it possible to work with these small concentrations while guaranteeing the homogeneity of dosage unit distribution.

Disintegrants

The term "disintegrant" or "disintegrating agent" indicates a substance whose role is to accelerate the disintegration of a tablet and thus the dispersion of the active principle in the dissolution medium (aqueous medium or gastric juices, for example). These agents are used as adjuvants in tablet formulations in order to support the disintegration thereof and the release of the active principle. In general, they are extremely hydrophilic agents often exhibiting the property of swelling quickly in contact with water, in which the hydration and/or the swelling and the increase in volume causes the disintegration of the tablets containing them.

Matrix Tablets and Tablets Having a Polymer Network

By "matrix tablets" is meant tablets in which the active principle is mixed closely with the polymer. This type of tablet is used classically for the production of extended-release tablets, for example. This limited association is responsible for a modification of the behavior of the active principle in the dissolution medium. Indeed, the behavior of the active principle will be strongly influenced by the behavior of the constitutive polymer of the matrix in the presence of water.

Matrix tablets are obtained classically either by the simple mixture of powders, or by granulation in order to improve the properties of the mixture before compression. In the present application, "matrix tablets" is used to indicate these types of tablets obtained by the simple mixture of powders, and "matrix effect" is used to indicate a dissolution profile similar to that obtained from a classical matrix tablet.

The tablets in conformity with the invention have, on the contrary, a multiparticulate structure because they are obtained by the direct compression of the microgranules. They have the advantage of exhibiting a matrix effect without exhibiting the disadvantages of classical matrix tablets.

In the present application, "in situ matrix" is used to describe the polymeric network formed within the tablets of the invention, following the compression of the microgranules, and "tablets having a polymer network" is used to describe the tablets in conformity with the invention.

Modified Release

In the present application, the term "modified release" is used to indicate a release profile of the active principle that is modified compared to that which the active principle alone would have exhibited in the dissolution medium. In the present invention, the modification of the profile is due to the use of a polymer whose nature will lead either to an acceleration of the release of the active principle, referred to as accelerated release, or to a delay in the release of the active principle, referred to as delayed release, or to an extension of the release of the active principle, referred to as extended release.

The aim of the present invention is to provide a novel oral pharmaceutical composition based on tablets exhibiting a matrix effect, that is, a behavior in the dissolution medium similar to that of matrix tablets. Such tablets thus make it possible to envisage either a modified release of the active principle in the organism, or a rapid disintegration of the tablet as a function of the nature of the polymer used, even for very low doses of active principles.

The present invention relates to tablets obtained by the direct compression of microgranules comprised of three distinct parts. These microgranules are thus comprised, from the center towards the periphery, by a neutral support, preferentially a core of sugar and corn starch, then by an intermediate polymeric layer lacking the active principle and comprising at least one polymer of interest, that is, a polymer whose properties are to be exploited to influence the release profile of the active principle, and finally by an active layer comprising the active principle or principles themselves.

Forms with Extended Release

The solid dosage forms with extended release can be classified in two major categories: forms termed "reservoir" in which the active principle is maintained inside a compartment delimited by a membrane that slows its diffusion, and forms termed "matrix" in which the active principle is mixed homogeneously within a polymeric matrix that slows or accelerates its diffusion.

Reservoir-type extended-release tablets generally consist of a mixture containing the active principle coated with a diffusional film that prolongs the release of the active principle in the dissolution medium. These are referred to as film-coated tablets. In this case, the film covers the tablet uniformly.

This type of film-coated tablet is used classically in the pharmaceutical industry to modify the release profile of the active principle and/or to protect it.

A specific case relates to reservoir-type extended-release tablets which can be comprised of microgranules coated with an external layer that regulates the diffusion of the active principle in the dissolution medium. These microgranules are subjected directly to the stresses of compression. Indeed, obtaining tablets that are sufficiently cohesive to be manipulated requires the application to the microgranules of a relatively high compression force. The physical stresses exerted on the microgranules are often responsible for a deterioration of the external layer responsible for the extended release. As a result the release profile is modified, which leads to a release of the active principle that is more rapid than expected, and is in any event unpredictable and thus not reproducible.

To overcome these disadvantages, several specific compositions have been developed. Thus, patent EP 1032374 describes a pharmaceutical composition containing deformable spheroids, whose external film resists compression stress while becoming deformed without rupturing. However, such a system is relatively complex and requires the use of several specific polymers and, in particular, of thermoplastic excipients.

The systems known as matrix systems are, on the other hand, often much simpler to manufacture. Indeed, in such compositions, the active principle is simply mixed with the polymer, within a polymeric matrix.

The polymeric matrices can be of hydrophilic nature, that is, comprised of polymers exhibiting high affinity for water. Such matrices generally ensure the extended release of the active principle by forming, in contact with the surrounding aqueous medium, a gel which, by its swelling kinetics, erosion kinetics or its capacity to play a role as a diffusional barrier, extends the release of the active principle in the dissolution medium.

Thus, the Nostrum Pharmaceutical patent U.S. Pat. No. 6,416,786 describes extended-release tablets comprised of a hydrophilic matrix comprised of a mixture of a hydrocolloid such as xanthan gum with a cellulose ether. Such a mixture provides the composition with a synergistic extended effect due to the combined action of two polymers. Indeed, the hydrophilic character of xanthan gum produces the formation of the gel in contact with the aqueous medium more rapidly, the cellulose ether guarantees the gel a certain maintenance over time, and the xanthan gum used alone tends to erode rapidly in the dissolution medium.

Similarly, the Valentine Enterprises patent U.S. Pat. No. 5,292,534 describes an extended-release formulation of niacin and xanthan gum, this formulation being able to be provided as hard gelatin capsules or as tablets. The active principle is mixed closely with xanthan gum.

However, such mixtures are not suitable for a low-dose form. Indeed, the primary disadvantage of the classical matrix tablets manufactured from a mixture of powders of different natures is that the higher the weight ratio between the polymer powder and the active principle powder, the greater the risk of content inhomogeneity. Indeed, because of the differences of size, form and density of the excipient particles and the active principle particles, the mixture of the two powders is likely to generate a phenomenon of imperfect mixture or of particle segregation. Particle segregation corresponds to the separation of powders of different natures which intervenes in particular following the movements imposed on the mixture, for example during the transport or the manipulation of the powder mixture on an industrial scale.

This phenomenon inevitably leads to an inhomogeneity of distribution of active principle within the mixture. On an industrial scale, such an inhomogeneity leads to variations in the active principle content which can be very great from one tablet to another and which must be made the object of very specific control. This phenomenon is accentuated quite clearly when the proportion of the active principle decreases in the mixture.

In addition, another disadvantage often encountered for the matrix tablet forms is the need for granulating all or part of the constituents before the compression step. This pregranulation makes the process longer and more complex than with only one direct compression step.

Rapid Disintegration Forms

The rapid disintegration tablets of the prior art are generally comprised of a mixture of excipients and of active principle, when direct compression of this mixture is appropriate or from granules containing the active principle, obtained after granulation, for example, then compressed, after the mixing of an external phase, comprising the disintegrant when direct compression is not possible.

Thus, in the patent EP 548356 the granules coated with active principles are assembled by compression after having been mixed beforehand within a compression matrix comprised of, among other things, a direct compression sugar required in this step of the process.

Such tablets are no longer suitable for the delivery of low-dose active principles. Indeed, here again is presented the problem of particle segregation of powders of different natures which makes it quite delicate to obtain tablets that are homogeneous and of low dose.

The patent U.S. Pat. No. 5,607,697 describes tablets with rapid disintegration that lack the compression matrix, wherein the active principle is simply granulated with a compression excipient. These granules are then coated and compressed. However, even in this type of method without a matrix, the compression excipient is mixed in way in which it is difficult to control the active principle. Thus, this type of formulation does not make it possible to ensure a homogeneity of content that is sufficient for low-dose active principles.

Thus, the primary disadvantage of the extended-release matrix tablets and the classical rapid-disintegration tablets is that they are poorly adapted as a support for low-dose or very low-dose active principles for which the homogeneity of content is paramount and imperative.

However, the manufacture of low-dose tablets which overcomes these problems of particle segregation and content inhomogeneity when the ratio between the active principle and the other excipients is very low has already been the object of study.

Thus, the Ethypharm patent EP 1200071 describes tablets of low-dose in active principle, obtained by the direct compression of simple neutral cores or "sugar spheres" on which have been sprayed beforehand a solution of active principle capable of containing a binding agent. Such tablets have the advantage of exhibiting a high homogeneity of active principle content and a high reproducibility, even at very low concentrations of the active principle.

In addition, such tablets do not require specific compression excipients and they can be subjected to a direct compression step. However, these tablets do not make it possible to envisage a modified release of the active principle, and the release of the active principles in the medium is immediate to quasi-immediate, except if the tablet has been coated, as is the case with the reservoir forms.

Thus, the matrix tablets of the prior art which allow a modified release of the active principle do not make it possible to envisage the incorporation of low-dose active principles, and in addition, the tablets exhibiting this quality are not suitable for a modified release of the active principle.

This is why the solution provided by the present invention to the technical problem is based on the production of tablets exhibiting a matrix effect, while avoiding the disadvantages related to the manufacture of this type of tablet, in particular the difficulty of obtaining low-dose matrix tablets exhibiting a homogeneous content in active principle.

The behavior in the organism of the active principle contained in such tablets will thus depend on the nature of the polymer or polymers comprising the polymeric matrix or the polymeric network.

Advantages of the Tablets of the Present Invention

The present invention presents several advantages compared to the formulations of the prior art.

First, the tablets in conformity with the invention are of a relatively simple structure and can be easily implemented in the pharmaceutical industry by a method that is simple, reproducible, relatively inexpensive and of high yield in all of the manufacturing steps as described below.

On the one hand, the method according to the invention does not comprise any granulation or pre-granulation step necessary for the compression of the majority of the mixtures of excipients in the form of powder.

On the other hand, the direct compression step itself is advantageously carried out without compression excipients with the exception of a possible conventional lubricant used in a small quantity, in any event at less than 5% by weight of the final weight of the tablet. This latter characteristic is due in particular to the excellent compression behavior of the microgranules comprising the tablets in conformity with the invention.

Another advantage of the invention is that it makes possible the manufacture of extended-release or rapid-disintegration tablets starting from a very small quantity of polymer, which reduces both the cost of the method and time necessary for its implementation.

The method in conformity with the invention is in addition highly reproducible which thus makes it possible to envisage the industrial production of such tablets while satisfying the regulatory requirements of the pharmaceutical industry with regard to the quality and to the conformity of the medicament, in particular with regard to the homogeneity of the weight and of the content of the tablets, as is shown in table 7. This table also shows the quality of the method in terms of yield, since for each of the three batches exemplified the overall yield by weight is always greater than 90%.

Another advantage of the tablets according to the invention is that they exhibit a high homogeneity, not only of form, of size, and of density, but in addition of content in active principle, even at very low doses, that is, doses lower than 50 mg, preferentially lower than 25 mg, or even lower than 10 mg per tablet.

In addition, because of this structural homogeneity, the risk of microgranule segregation during the manufacture of the tablet is very low, which decreases both the risks of inhomogeneity of content between the tablets and even between two halves of a scored tablet.

This latter aspect is particularly important insofar as the classical matrix tablets are in general not at all suitable for scored forms.

It is easily understood that in the case of the reservoir-type tablets, the scored form is not possible because the continuity of the diffusional film cannot be ruptured. In the case of matrix tablets, and in particular of polymeric matrix tablets, on the one hand even the structure of the tablet does not lend itself to a distinct cut of the tablet, and on the other hand, the homogeneity of the active principle content between the two halves of the tablet is not guaranteed.

On the contrary, in the tablets of the invention, the homogeneity of the content is ensured by the precise distribution of the active principle on the surface of the neutral microgranules, even at low doses. The small size of the microgranules allows a balanced and precise weight distribution for the two halves of the tablet when sectioned. Thus, the tablets according to the invention can be most certainly be envisaged in a scored form.

In addition, the tablets in conformity with the invention can most certainly be coated, after the steps of the method described below, with one or more additional layers of film coating intended to further modify the release profile of the active principle. Indeed, the tablets in conformity with the invention are, at the end of the manufacturing method, quite similar to classical tablets and thus can, without any difficulty, receive a film coating suitable for the needs. This film coating can be applied for the purpose of protecting the active principle, of conferring a gastroresistant release profile or of masking the taste of the active principle, for example.

It can be anticipated, for example, to film-coat the tablets in conformity with the invention with one or more layers of a gastroresistant film-coating agent in order to limit the release of the active principle at the gastric level.

Moreover, the components required for the production of the tablets in conformity with the invention are at the same time approved for pharmaceutical use, inexpensive, and with respect to the polymer of interest, required in a relatively small quantity as described below.

Lastly, the aforementioned tablets are usable for all types of active principles, and more particularly for the active principles whose action on the organism is very powerful, and thus which must be administered at a very low dose and be released in a progressive manner, or conversely in an accelerated manner, in the organism. For example, hormones or their derivatives, active principles acting on the central nervous system or the cardiovascular system, antibiotics, antivirals, analgesics and anti-inflammatories drugs are particularly usable in the tablets of the invention.

In addition, the tablets of the present invention are also particularly suitable for the administration of active principles whose therapeutic range is very narrow. Indeed, in this case, it is of paramount importance to be able to administer with certainty a very precise dose of the medicament. Thus, the excellent qualities of homogeneity of weight and of content of the tablets in conformity with the invention make them quite suited to this type of delicate administration.

The present invention relates to tablets, usable in the pharmaceutical industry for the administration of active principles, which allow a modified release. In particular, the tablets in conformity with the invention are particularly suitable for the administration of low-dose active principles.

The present invention has as an object low-dose tablets obtained by the direct compression of microgranules which are essentially comprised of a neutral support, coated with a polymeric layer comprising at least one pharmaceutically acceptable polymer and allowing the modified release of the active principle in an aqueous medium lacking the active principle, to which is applied an active layer comprised of at least one active principle.

These tablets have the advantage of containing the active principle distributed homogeneously. These tablets can thus be provided in scored form.

The present invention also has as an object the intermediate products able to be used for the preparation of the tablets. These intermediates are:
- the functionalized excipient comprised of a neutral support coated with a polymeric layer comprising at least one pharmaceutically acceptable polymer and allowing the modified release of the active principles in an aqueous medium,
- the microgranule comprised of a neutral support coated with a polymeric layer comprising at least one pharmaceutically acceptable polymer and allowing the modified release of the active principles in an aqueous medium, to which is applied an active layer containing at least one active principle.

The microgranules according to the invention have a size between 50 µm and 3000 µm, approximately.

The polymeric layer can contain in addition at least one pharmaceutically acceptable binding agent. Preferably, a binding agent of hydrophilic nature that dissolves easily in water and/or in ethanol will be used. Thus, for example, polyvinylpyrrolidone, in particular the polyvinylpyrrolidone sold under the brand name PVP K30®, is used as a binding agent in the polymeric layer.

The polymeric layer can contain in addition a wax or a derivative thereof, or a derivative of fatty acids of glycerol, or a mixture thereof.

For example, natural or purified beeswax can be used.

The glycerol fatty acid esters and the derivatives thereof can be selected among glycerol monostearate, glycerol monooleate and glycerol palmitostearate for example, but also among the mixtures of the fatty acid esters and glycerides of polyethylene glycol, such as those belonging to the lauroyl macrogolglycerides family sold under the brand name Gelucire®.

Advantageously, the polymer that is pharmaceutically acceptable and that allows the modified release of the active principles in an aqueous medium, which is contained in the polymeric layer, represents from 1% to 100% by weight of the weight of the neutral support, preferably 1% to 50% by weight of the weight of the neutral support.

The Neutral Support

The aforementioned neutral support upon which the microgranules of the invention are based is preferably a microsphere comprised of sucrose and of corn starch, of a size between 50 µm and 3000 µm, preferably between 100 µm and 1000 µm, and more preferentially still between 100 µm and 500 µm.

These microspheres, used routinely in the pharmaceutical industry, are defined in the European Pharmacopeia under the term "sugar spheres."

These "neutrals" are advantageously usable as a base support for the functionalized excipients referred to above, in particular because of their great homogeneity of weight, of size, of form and of specific surface, which makes them a tool of choice for the manufacture of low-dose medicaments obtained by spraying and for which the perfect homogeneity of the batches with respect to the content in active principle must be ensured.

In addition, as has been shown in patent EP 1200071, neutrals are the excipients of choice for tabletting systems. In particular, the "sugar spheres" have shown an excellent behavior in direct compression, all the more interesting as these neutrals can be compressed without other compression excipients, with the exception of a lubricant in a very small quantity.

The Polymers of Interest

The "matrix" effect observed with the tablets in conformity with the invention, that is, their propensity to behave as conventional matrix tablets in which the polymer and the active principle have been mixed homogeneously, is due to the compression step which generates a specific structure by allowing, in an unexpected way, the creation of a matrix "in situ." Such a matrix is formed indeed only at the time of the compression.

In such a configuration, the active principle is then trapped in a true polymer network comprised of the various polymeric layers of the adjacent microgranules.

Indeed, a polymer network, which will be preferentially continuous for extended-release tablets, forms around the active principle during compression.

Thus, starting from a certain concentration threshold of the polymer, the deformation of the polymer granules deposited on the surface of the neutral microgranules, following the crushing stress exerted by the compression forces, can allow the creation of a polymer network. The compression contributes to the deformation and to the elongation of the polymer granules which end up entering in close contact with each other, thus creating a true network observable only from a critical quantity of the polymer, corresponding to the concentration threshold.

In the case of the use of polymers intended to extend the release profile of the active principle, the concentration threshold required for the creation of an "in situ" matrix is reached as soon as a network known as a "percolation network" is formed, corresponding to a continuous network of the polymer particles, following the compression step. The formation of such a network between the microgranules is responsible for an extended release of the active principle from the core of this complex. The diagrams of FIG. 5 allow a good understanding of the phenomenon of flattening and of creation of the continuous network following the compression step.

In the case of the use of disintegrating polymers, obtaining a percolation network is not required, because the matrix effect is observed as soon as a network, even discontinuous of polymer particles, is formed at the end of the compression step. Such a discontinuous network is sufficient to ensure the rapid penetration of water within the tablet thus formed, because of the strong affinity for water of the disintegrating polymer particles. This hydration leads to an abrupt swelling and thus to a rapid disintegration of the tablet after its contact with the aqueous medium.

Indeed, contrary to the case of the bulk granules (see FIG. 4), once compression is carried out, each layer of active principle is in contact with the layer of active principle of the neighboring microgranule. This double layer of active principle will thus be enclosed between two layers of the polymer, except on the external surface of the tablet. This is referred to as a "sandwich" structure.

Thus the polymer of interest remains particularly well localized not only with respect to the active principle, because the polymer/active principle contact is very high on the developed surface, but also on the level of the tablet: the structure and the composition of the tablet are very homogeneous. Thus are obtained tablets comprised of multiple layers of the active principle, each being sandwiched between two layers of the selected polymer. Consequently, on the level of the tablet, the components are ideally positioned: the double layer of the active principle is located sandwiched between two layers of the polymer modifying the release of the active principle during the contact with the dissolution media.

Thus, if a polymer used in a classical way for the constitution of extended-release matrix tablets is used as the polymer of interest, an extended-release tablet will be obtained.

If, on the contrary, an excipient used in a classical way for the disintegration of tablets is used as the polymer, a tablet with rapid disintegration will be obtained, one which allows a rapid dissolution of the active principle in the dissolution medium, a dissolution that is all the more easy if the excipient support ("sugar spheres") is hydrophilic and highly water soluble.

The behavior of the tablet during its contact with the dissolution medium will thus be a function of the behavior of the polymer forming this network or this matrix.

Thus are understood the multiple advantages of the invention which follow from the fact of the ability to adapt the polymer to the application envisaged in an extremely simple way. Indeed, the neutral microgranules which form the support of the tablets in conformity with the invention preserve their good compression behavior whichever the type of polymer deposited on their surface, even if these properties can be seen to change in certain cases and must be adjusted by the specifics of the formulation. In addition, the tablets according to the invention make it possible to work with a wide range of polymers as well as of active principles, all while guaranteeing a perfect homogeneity of the content in active principle, and in particular at very low doses.

The polymer contained in the polymeric layer of the microgranules comprising the tablets that are the object of the present invention is preferably selected among the extended-release polymers and the disintegrating polymers.

Disintegrating Polymers

The polymers used in the present invention to favor the disintegration of the tablet, and thus the rapid dispersion of the active principle in the dissolution medium, are polymers generally used for their capacity to rapidly swell in contact with water thus leading to a bursting of the tablet which contains them.

The disintegrating polymers are advantageously selected among polyvinylpyrrolidone derivatives, starch derivatives, calcium and magnesium salts and carboxymethylcellulose derivatives, as well as the mixtures thereof.

The polyvinylpyrrolidone derivatives can be selected among crospovidone or povidone.

The starch-derivative polymers can be selected among sodium carboxymethyl starch, such as that sold under the brand name Explotab®, for example, or cross-linked starch.

The cellulose derivatives can be selected among sodium carboxymethylcellulose or croscarmellose sodium, such as that sold under the brand name Ac-Di-Sol®, for example, methyl cellulose or low-substituted hydroxypropylcellulose, for example.

All of these polymers can be applied by powdering on the surface of the neutral microgranules in the same way as for the extended-release polymers as is described in detail in the method below.

Polymers for Extended Release

With respect to polymers of a hydrophilic nature, polymers with gelling properties will be selected advantageously, and preferentially, polymers of a viscosity higher than 1000 mPa·s (millipascal second) measured in a 2% w/w aqueous solution at 20° C., according to the European or the American Pharmacopeia, will be selected.

The polymers with gelling properties have the property of quickly forming upon contact with the aqueous medium a viscous gel by swelling, called hydrogel swelling, which extends the release of the active principle in this medium. The highly hydrophilic polymers, exhibiting capacities of rapid hydration and thus of rapid swelling with the formation of a gel, will be used preferentially because they lead to a diffusional mode of release.

Indeed, three major mechanisms are considered to be responsible for the degradation of the gel and thus for the extended release of the active principle contained in the gel toward the dissolution medium: a swelling phenomenon, a diffusion phenomenon and an erosion phenomenon.

Swelling is the hydrogel formation step corresponding to the hydration of the polymer. The release of the active principles is thus determined by the swelling rate. Indeed, as long as the hydrogel is not formed the active principles can neither be released by erosion nor by diffusion. The swelling kinetics are thus a limiting factor in the release of the active principle.

Erosion being a relatively unforeseeable phenomenon, it is preferable for the extended release of the medicament to have recourse to a primarily diffusional release system. Thus, hydrophilic polymers with gelling properties are good candidates for this type of system. The release rate of the active principle can indeed be adjusted according to the density and thickness of the gel formed in the aqueous medium.

The extended-release polymers of hydrophilic nature are preferably selected among the polymers derived from cellulose, the natural or modified natural polysaccharides such as the gums, the galactomannans, the glucomannans, the succinoglycans or the scleroglucans, the carbomers and the poly (ethylene oxides), as well as the mixtures thereof.

Polymers derived from cellulose, in particular the semi-synthetic derivatives of the group of cellulose ethers of medium to high viscosity, such as those classically used for the constitution of hydrophilic matrices that extend the release of the active principle, are used, for example.

The cellulose derivatives can be selected among hydroxyethylcellulose (HEC), hydroxypropylcellulose (HPC) and hydroxypropylmethylcellulose (HPMC).

The carbomers able to be used are, for example, those of brand name Carbopol® 971P, Carbopol® 974P or Carbopol® 934P.

The natural or modified natural polysaccharides can be selected among the gums, the galactomannans, the glucomannans, the succinoglycans and the scleroglucans.

The polymers belonging to the group of the poly(ethylene oxides) can be selected among those of brand name Polyox WSR®.

In a preferential way, the polymers of a hydrophilic nature exhibiting gelling properties according to the invention belong to the category of gums, in particular of gums of natural or microbial origin, such as alginic acid, the alginates, in particular sodium alginate, agar-agar, the carrageenans, carob gum, gum guar, gum tragacanth, gum arabic, cassia gum, xanthan gum, gum karaya, tara gum and gellan gum.

In a preferred way, gums of bacterial origin, in particular xanthan gum, will be used in the carrying out of the present invention.

Xanthan gum is a natural polysaccharide of bacterial origin arising from the fermentation of corn starch by the bacterium *Xanthomonas campestris*. This biopolymer of high molecular weight is comprised of multiple repeating units, each containing five molecules of monosaccharides: two molecules of glucose, two molecules of mannose and one molecule of glucuronic acid. In the solid state, xanthan gum appears as a powder whose particles have a size of between 10 µm and 180 µm, approximately, and, according to the grade, a relatively spherical shape.

Advantageously, the hydrophilic polymer with gelling properties in conformity with the present invention accounts for 1% to 100% by weight of the weight of the neutral support, preferably 1% to 50% by weight of the weight of the neutral support.

Among the polymers of different natures, certain polymers and copolymers derived from methacrylic acid and insoluble in water regardless of pH can be used, in particular certain copolymers of methacrylic acid sold under the brand name Eudragit®, such as Eudragit® RS PO, Eudragit® RL PO, Eudragit® RL and Eudragit® RS, which belong to the family of poly(ethyl acrylate, methyl methacrylate, trimethylamonioethyl methacrylate) chlorides.

Certain cellulose polymers that are insoluble in water, such as ethylcellulose and cellulose acetate, and the mixtures thereof, can also be used.

Such polymers lead to an extended release of the active principle in the dissolution medium primarily by a mechanism of erosion. Indeed, their properties delay the penetration of water within the tablet, and the active principle is thus released as it enters in contact with the aqueous medium following the progressive erosion of the polymer matrix.

Certain mucoadhesive polymers can also be used, such as sodium carboxymethylcellulose, the carbomers, sodium alginate, hydroxyethylcellulose, hydroxypropylcellulose, hydroxypropylmethylcellulose, gelatin, guar gum, poly(ethylene oxide), dextrin or chitosan.

Such polymers are generally used to prepare tablets intended for sublingual or transmucosal administration.

All of the polymers described above can be applied by powdering on the surface of the neutral microgranules as is described in detail in the method below.

Mixture of Polymers of Different Natures

For the carrying out of the present invention it can be anticipated that the polymeric layer applied to the neutrals is comprised of a mixture of polymers of different natures, used either in synergy for obtaining a specific release profile or in complementarity to modify the dissolution profile and to provide an additional quality to the tablet.

The mixture of polymers comprising the polymeric layer must then be suitable for the qualities sought for the polymeric matrix, in particular, the proportion of each polymer will have to be adjusted to satisfy the constraints related to the expected release profile or the other functionalities described.

The Active Principle

The active layer of microgranules comprising the tablets in conformity with the invention includes a pharmaceutical active principle which can be of any nature.

The active layer can contain in addition at least one pharmaceutically acceptable binding agent.

For a simple carrying out of the invention, active principles that are soluble in water and/or in alcohol or in any other slightly- or non-toxic pharmaceutically acceptable solvent will be used. However, active principles that are slightly or very slightly soluble in these solvents can however be envisaged for the carrying out of the present invention, insofar as very low concentrations in the active principle are used preferably, concentrations for which the dissolution of the majority of these active principles can be envisaged.

Active principles acting at very low concentrations are particularly suitable for the tablets in conformity with the invention.

The tablets according to the present invention can comprise as an active principle the hormones or the derivatives thereof, for example, the active principles acting on the central nervous system, the active principles acting on the cardiovascular system, the antibiotics, the antivirals, the analgesics and the anti-inflammatories.

The active principles acting on the central nervous system are preferably selected among the anti-epileptics, the anti-Parkinson's drugs, the psychostimulants, the psychotropics, the antidepressants, the anxiolytics and the antipsychotics, for example. In particular, the tablets are particularly suitable for active principles such as risperidone, donepezil, physiostigmine, rivastigmine, buspirone, diazepam, fluoxetine, minalcipran, paroxetine, sertraline, venlafaxine, lamotrigine and tiagabine.

The active principles acting on the cardiovascular system are preferably selected among the antihypertensives, the antithrombotics, the anti-aggregating agents and the cholesterol-lowering agents. The tablets are particularly suitable for active principles such as fluvastatin, lovastatin, pravastatin, simvastatin, bezafibrate, ramipril, losartan, atenolol, carvedilol, metoprolol, nifedipine and furosemide.

The analgesics can be selected among hydrocodone, hydromorphone, morphine, oxycodone, oxymorphone, tramadol and gabapentin.

In an advantageous way, the active principles are integrated in the active layer in association with a pharmaceutically acceptable binding agent, such as that usually used in the pharmaceutical industry for the binding of active principles to the surface of neutral supports. Thus, the method of the binding of the active layer described in patent EP 1200071 can certainly be used for the binding of the active layer within the framework of the present invention.

In a preferred way, the active layer of the microgranules in conformity with the invention is applied by the spraying of a solution of the active principle in a solvent (called the layering solution), that is, a quite homogeneous dispersion of the active principle on a molecular level. Advantageously, this solution also contains the binding agent.

Among the pharmaceutically acceptable binding agents, binding agents of a hydrophilic nature, in particular cellulose derivatives such as HPMC, in particular the grades Pharmacoat® 603 and Pharmacoat® 606, polyvinylpyrrolidone derivatives, in particular the grade PVP K 30, and also polyethylene glycol derivatives will be used preferentially. In particular, polyethylene glycol of a molecular weight in the range between 3000 and 7000, such as PEG4000 and PEG6000 in particular, will be used as a binding agent.

The solvent of the sprayed layering solution must be suitable for the active principle or for the mixture of active principles used. Thus, for example, water, ethanol or hydroalcoholic solutions of various concentrations can be used for the creation of the base solution of the active layer. As far as possible, it will be sought to adapt the solvent to the nature and to the physicochemical properties of the active principle in order to limit the volume of the solution required for the dissolution of the active principle. However, insofar as the present invention is applicable to low-dose or very low-dose tablets, the constraint imposed by too-high dissolution volumes remains marginal.

To the extent possible, it is preferable to use solvents that are non-toxic and easily eliminated by evaporation during drying so that no traces of them remain in the tablets.

The specific structure of the microgranules according to the invention and the direct compression step applied to these microgranules make it possible to obtain a modified release profile for the active principle, a profile directly related to the nature of the polymer used (see FIGS. 1, 2, 3 and 4).

The phenomenon of modified release observed by the applicant according to the nature and to the qualities of the polymer used depends on the compression step, but it also depends on the type and quantity of the polymer used.

The present invention thus makes it possible to easily adapt the nature as well as the quantity of the polymer used for obtaining the release profile sought. Indeed, whether the polymer of interest is a polymer that slows the release of the active principle such as xanthan gum, for example, or whether it is a disintegrating polymer such as crospovidone, the release profile of the active principle will be similar to that observed for classical matrix tablets obtained from these different polymers.

Film-coating Agents

It can be certainly be anticipated, taking into account their similar physical characteristics to those of classical tablets, to coat the tablets in conformity with the invention with one or more additional layers of one or more film-coating agents, according to the way in which the release profile of the active principle is sought to be modified.

If it is envisaged to confer a gastroresistant release profile on the tablets according to the invention, it can be certainly anticipated to film-coat them classically with one or more layers according to the needs of one or more gastroresistant film-coating agents.

For this type of film coating all of the excipients classically known by those skilled in the art for these qualities can be used, such as certain polymers derived from methacrylic acid, and in particular the copolymers of methacrylic acid sold under the brand name Eudragit® L whose chemical name is poly(methacrylic acid, ethylacrylate), or certain derivatives of cellulose such as hydroxypropylmethyl cellulose phthalate, for example, or certain derivatives of polyvinyl acetate such as polyvinyl acetate phthalate. On the tablets according to the invention can also be conferred a colonic release by using certain polymers derived from methacrylic acid, and in particular the copolymers of methacrylic acid sold under the brand name Eudragit® S and Eudragit® FS whose chemical name is poly(methacrylic acid, methyl methacrylate).

The Method of Preparation of the Tablets

The present invention in addition has as an object the method of preparation of the tablets previously described comprising the following steps:
 the neutral support is moistened beforehand using a dampening solution possibly containing a binding agent;
 the polymer is then applied to the surface of the neutral support by powdering;
 the polymeric layer thus obtained is possibly dried to form a functionalized excipient;
 an layering solution comprising the active principle and possibly a binding agent are sprayed on the surface of the polymeric layer;
 the microgranules thus obtained are then dried, then directly compressed;
 the tablet thus obtained is possibly coated with one or more layers of a film-coating agent.

In addition, the compression step can be carried out using a lubricant at less than 5% by weight compared to the total weight of the tablet.

Method of Application of the Polymeric Layer by Powdering in a Conventional Coating Pan The placing in solution of polymers, and in particular of hydrophilic gelling polymers, such as polysaccharides of high molecular weight, inevitably involves the problem of the viscosity of the layering solutions: only small quantities of the polymer can be dissolved and then applied in an air fluidized bed except to obtain volumes of the layering solution that are incompatible with an industrial implementation of the method. The polymer concentration is thus a limiting factor for certain polymers if an application of the polymeric layer by spraying is envisaged.

Thus, for the carrying out of the present invention, the step of the binding of the polymeric layer is preferentially carried out by powdering, which makes it possible to increase the quantity of the polymer to be bound on the neutrals while avoiding the problems of viscosity encountered with many polymers.

In addition, it can be anticipated to associate with the polymer of the polymeric layer a wax or a derivative thereof, or a glycerol fatty acid derivative, or a mixture thereof.

This method consists of carrying out the application of the polymer in dry powder form on the neutral microgranules in a conventional coating pan, using a dampening solution. The active layer containing the active principle with a possible binding agent can then, in a classical way, be applied by spraying in an air fluidized bed or using other conventional application devices.

The conventional coating pan used for the application of the polymeric layer is, for example, a container of spherical shape open over a quarter of its surface and inclined compared to the horizontal. The application of the polymer is carried out manually, possibly using a binder dissolved in a solvent. In a preferred way, a slightly- or non-toxic solvent is used, such as water, ethanol or a hydroalcoholic solution. This solution, known as a "dampening" solution, is used to moisten the neutral cores and to favor the binding of the polymer powder on their surface.

The application cycle is, for example, the following:
 First, the mass of the neutrals in rotation in the coating pan are dampened by the application of a thin layer of dampening solution on the surface of the neutrals.
 Then the step of the powdering of the mass of neutrals is carried out by the manual dispersion of a certain quantity of the polymer of interest on the surface of the neutrals.

The polymer is thus bound to the surface of the neutral support in the form of powder granules.

The powdering operation is renewed as many times as is required to obtain a "functionalized excipient" of the desired content in polymer. Thus, a variable number of dampening/powdering cycles proceeds depending on the quantity of the polymer of interest selected.

The advantage of the application in a conventional coating pan lies in the fact that the polymer is projected in dry form and thus no gelation phenomenon occurs. Thus are avoided the technical problems, such as the clogging of the spraying tubes or the agglomeration of the neutral granules, observed during the spraying of viscous polymers.

For a homogeneous distribution of the polymer on the surface of the neutrals it is preferable that the neutrals/polymer granules size ratio is not too low, which is why neutrals of a size greater than 50 µm will preferably be used.

Lastly, a drying step makes it possible to eliminate the solvent used during the step of the dampening of the neutrals. Preferentially this operation is carried out externally, that is, a temperature-controlled air blower heats the wall of the coating pan which transmits heat by conduction to the neutrals, themselves in agitation.

Drying can also be carried out in an air fluidized bed or an oven or according to any other means of drying usually used for the drying of microgranules. The drying operation can last several hours until the complete drying of the assembled microgranules. The temperature in the coating pan is maintained at a constant, generally lower than 80° C., for a temperature within the mass of the neutrals ideally near 40° C.

Thus, at the end of these steps, a stabilized "functionalized excipient" is obtained, that is, a neutral support on which the selected polymer of interest is bound in a stable fashion.

FIG. 6 is an electronic microscopy photograph of the microgranules in conformity with the invention after the polymer powdering step.

This takes on a quite specific importance in terms of industrial manufacturing, since it can be quite envisaged to manufacture these excipients independently and to store them and/or to transport them to the location where they will receive the active layer in conformity with the present invention before being compressed. The functionalized excipients of the present invention thus exhibit a considerable ease of use in industrial terms.

Preparation of the Layering Solution

The step of the application of the active layer in accordance with the present invention makes it possible to obtain low-dose microgranules whose content in the active principle is at the same time precise and uniform. In particular are avoided the problems of particle segregation before the direct compression step by the application on the neutral cores coated beforehand with a polymeric layer of the active principle in dissolved form in the layering solution, which makes it possible to solidify the mixture without granulation.

The layering solution is the solution in which the active principle(s) will be dissolved or placed in suspension (dispersed) and which will be sprayed on the surface of the "assembled" microgranules, referred to as "functionalized excipients" in the present application. This solution contains advantageously an evenly-dissolving conventional binding agent.

If the active principle is dissolved, the solubility of the active principles during the preparation of the layering solution must be taken into account. Indeed, it must be made sure that the active principle is completely dissolved before carrying out its spraying. Thus, the quantity of the layering solution is advantageously selected as being equal to at least 1.5 times the quantity required to reach the saturation concentration of the active principle.

Application of the Active Layer

The active principle is applied to the "powdered" granules, that is, coated with the polymer of interest, in a conventional way by spraying, in an air fluidized bed, for example. Generally, this method rests on the simultaneous spraying through a tube of the active principle(s) and possibly a binder which are perfectly dissolved or dispersed in the layering solution, which guarantees for this step of the method a perfect homogeneity of content.

The time required for the application is highly variable and depends on the quantity of the active principle to pulverize and on its solubility in the layering solution. In a general way it is between 1 hour and 10 hours.

At the end of the application step, the microgranules are dried in an air fluidized bed and then filtered before the direct compression step.

Thus, the time required to carry out the method is a function of the quantity of the polymer to be applied, but also of the quantity of the active principles to be sprayed and the solubility of the active principle in the application solvent. This is why it is useful to adapt the layering solution to the conditions of the solubility of the active principle, in order to decrease the volumes of the solution to be sprayed and thus the time required for the application step. This method can generally be broken down in the following way:

Phase 1: Powdering: between 1 hour and 3 hours for the constitution of the polymeric layer.

Phase 2: Drying (elimination of the application solvent): between 0.5 hour and 12 hours depending on the quantity of solvent used.

Phase 3: Application: between 1 hour and 10 hours for the spraying of the solution of the active principle.

Phase 4: Drying between 15 minutes and 12 hours depending on the quantity of solvent used.

Phase 5: Direct compression of the microgranules thus obtained.

As has been mentioned previously, because of the stabilization of the functionalized excipient following the powdering step, it is quite possible to carry out the application and compression steps independently of the earlier steps (Phases 1 and 2). This characteristic makes it possible to envisage the easy transport and handling of the functionalized excipients obtained at the end of the first two steps of the method.

Compression

Before the compression step, the assembled microgranules are preferentially lubricated using a conventional lubricant, such as magnesium stearate, for example. The lubricant is used in general in a very small quantity, and generally at less than 5% by weight of the final weight of the tablet. The microgranules and the lubricant, for example, are mixed in a conventional way in a rotary mixer.

The compression itself can be carried out on an alternative press or a rotary press. The compression forces applied are preferentially between 50 MPa (megapascal) and 500 MPa. The compression step is not limiting: thus strong compression stresses can be applied without the risk of altering the structure of the tablet as it is in the case of "reservoir" systems. Indeed, not only do the neutral microgranules have an excellent compression behavior, as has been described in patent EP 1200071, but also the configuration of the microgranules in conformity with the invention is particularly suitable for high compression forces.

Of course, the compression stresses must however be suitable for the hardness and the cohesion sought for the tablets according to the invention.

Dissolution and Dosage Tests

Generally, the conditions of dosage and of dissolution of the tablets in conformity with the invention are those prescribed by the various European, American and Japanese Pharmacopeias.

Thus, to determine the release kinetics of the various systems studied, a conventional paddle or basket dissolution apparatus can be used. This apparatus can be connected to a spectrophotometer, able automatically to sample and to measure the UV absorbance of the solutions tested. This automatic measurement is only possible when the quantity of the active principle is sufficiently high and when the active principle does not absorb UV at the same wavelength as one of the excipients of the solution. This automatic measurement of UV absorbance makes it possible to determine, compared to a reference solution of known concentration, the quantity of the active principle released in the dissolution medium.

Such automatic sampling of the dissolution medium during the kinetics can be carried out in the following way:
- a sampling every 5 minutes during the first hour;
- a sampling every 15 minutes until the appearance of a plateau for 100% of the dissolved active principle.

When conditions do not lend themselves to this procedure, the dosage of the active principle released in the dissolution medium is carried out by samples taken manually which are then analyzed by HPLC (high-performance liquid chromatography).

Disintegration Tests

In the case of tablets manufactured from disintegrating polymers, a classical disintegration test will be used such as recommended by the European Pharmacopeia to judge rate of disintegration of the tablets in conformity with the invention.

In such a test, the tablets are placed in hollow cylindrical tubes at the bottom of which is a metal screen of a 2 mm mesh that retains the tablet inserted in each tube. The entire apparatus is submerged in a water bath. The tubes are then subjected to a regular, alternating vertical movement of approximately 30 cycles per minute.

The total disintegration time of the tablet is measured when no residue of the tablet remains on the surface of the screen.

The present invention also relates to the use of the tablets for the oral administration of medicaments, in particular for sublingual or transmucosal administration, when for example the polymeric layer contains mucoadhesive polymers. In particular, the tablets in conformity with the present invention are particularly useful for the administration of low-dose active principles, such as hormones and their derivatives, which must at times be administered at doses on the order of a microgram, but also vitamins and certain medicaments of the central nervous system or the cardiovascular system in particular.

BRIEF DESCRIPTION OF THE DRAWINGS

FIG. 5 represents the formation of percolation within the tablets during the increase in the quantity of the polymer (note: the effects of the compression of the neutrals are not taken in account).

EXAMPLES

A) Preparation of the Tablets

Example 1

Figure 1:
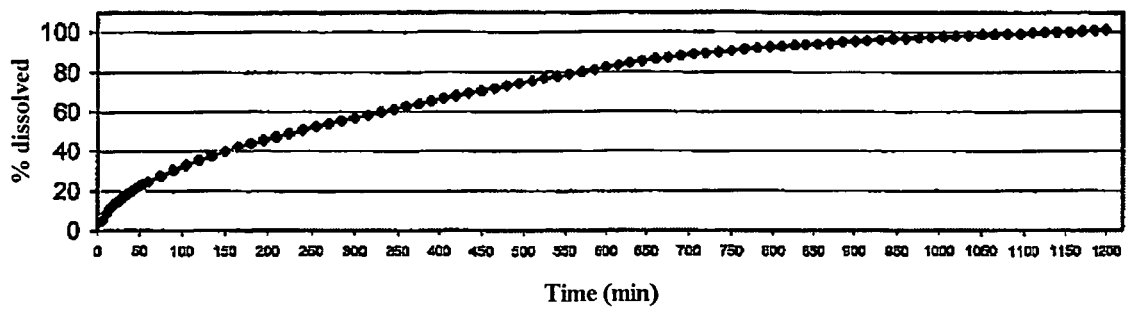
FIG. 1 represents the release profile of ketoprofen, used as the model active principle, obtained from tablets in conformity with the invention, obtained according to the method of example 1, whose polymeric layer comprises 5% by weight of xanthan gum (Rhodigel® 200 grade) compared to the weight of the neutral support.

Extended-release Tablets of Ketoprofen Microgranules with a 5% Xanthan Gum Base (Batch B4)

a) Application of the Xanthan Gum by Powdering

Two kilograms of neutral cores of a size between 400 μm and 500 μm (Suglets® provided by NP Pharm, France) on which will be applied the polymeric layer are introduced in a conventional coating pan and set in rotation.

The polymer used here is a hydrophilic polymer with gelling properties: xanthan gum (provided by Rhodia, France and sold as Rhodigel® 200 grade) of which 92% of the particles have a size less than 75 µm.

The neutral cores are first moistened using 300 grams of an alcohol solution of 15% polyvinylpyrrolidone (PVP K 30 grade, provided by ICI, France), which is 45 grams of PVP K 30.

This binding solution is applied by spraying on the surface of the neutrals in rotation via a manual sprayer.

5% by weight of the weight of the neutral microgranules, which is 100 grams, of xanthan gum in the form of dry powder are introduced manually in the coating pan in rotation immediately after the step of the moistening of the neutral cores.

These steps of moistening/powdering are carried out in several repeated cycles each comprising a first phase of the spraying of part of the polyvinylpyrrolidone solution on the surface of the neutral cores (moistening), followed by a phase of powdering corresponding to the projection of part of the xanthan gum powder.

The powdering operation lasts approximately 2 hours and comprises as many cycles of moistening/powdering as are required for the binding of the given quantity of xanthan gum. The rotation of the coating pan is maintained throughout the duration of the powdering phase.

At the end of the powdering operation, a step of the drying of the "powdered" neutrals is performed.

Drying is carried out by maintaining the mass of neutrals at constant temperature for 8 hours. The drying temperature is ideally approximately 40° C. within the mass of neutrals.

b) Application of the Active Layer

The neutrals applied with the polymeric layer of 5% xanthan gum are then subjected to the step of the application of the active principle. This step is carried out in an air fluidized bed (AFB) Kugelcoater® from Hüttlin (Germany), and the spraying parameters are summarized in table 1.

TABLE 1

Summary of the application parameters of the Huttlin air fluidized bed for the batch applied with 5% xanthan gum.

| | |
|---|---|
| Air intake temperature (° C.) | 50 |
| Air exhaust temperature (° C.) | 37 to 39 |
| Product temperature (° C.) | 38 to 40 |
| Atomization pressure (bar) | 0.8 |
| Air fluidization flow rate (m³/h) | 195 |
| Drying temperature (° C.) | 45 |
| Drying air flow rate (m³/h) | 195 |
| Drying time (min) | 30 |

The active principle used is ketoprofen (2-(3-benzylphenyl) propionic acid) provided by SIMS (Italy) at a concentration of 0.4% compared to the weight of the neutral cores, which is 8 grams for 2 kg of neutral cores.

Ketoprofen being virtually insoluble in deionized water (solubility less than 0.1 g/l according to the European Pharmacopeia), but having a pH-dependant solubility, a pH 8 buffer is used to allow its solubilization during the preparation of the layering solution.

The composition of the buffer medium is summarized in table 2.

TABLE 2

Composition of the buffer used for the dissolution of ketoprofen pH 8 buffer

| | |
|---|---|
| $KH_2PO_4$ | 6.805 g |
| Deionized $H_2O$ | 900 ml |
| 1 N NaOH | approx. 50 ml |
| (adjustment using a pH meter) | |
| Deionized $H_2O$ | qsp 1 l |

Ketoprofen is dissolved in the layering solution containing in addition as a binding agent polyethylene glycol of a molecular weight equal to 6000 ($PEG_{6000}$, ICI, France) also in dissolved form.

The binder is used in an amount of 5% by weight compared to the weight of the neutrals involved, which is 100 grams.

The layering solution is thus comprised of 2000 grams of pH 8 buffer in which 8 grams of ketoprofen and 100 grams of $PEG_{6000}$ are dissolved. This solution is sprayed on the surface of the microgranules according to the parameters recapitulated in table 1.

c) Drying and Screening

Once applied with the active principle, the microgranules are dried to eliminate any residual trace of the application solvent. The drying temperature is 45° C., applied continuously for 30 minutes.

At the end of the drying step, the microgranules are screened on a 0.625 mm screen in order to guarantee a perfect homogeneity of size within the batch.

d) Compression

Before compression, the assembled neutrals are lubricated with 0.125% w/w of magnesium stearate. Mixing is carried out in a Turbula® mixer for 2 min at 48 rpm.

Compression is carried out on the lubricated microgranules using a Frogerais OA instrumented alternative press mounted with flat punches 1 $cm^2$ in surface. The level of the filling of the matrix is adjusted to obtain tablets of approximately 500 mg in weight. The instrumentation and the associated software (Pecamec®, version 4.3, 2001, J2P Instrumentation) make it possible to make a continuous recording of the forces applied by the upper and lower punches, of the ejection and residual forces, as well as a recording of the displacements of the punches. The 250 MPa pressure stress applied makes it possible to have a sufficient cohesion of the tablets.

e) Dosage and Dissolution of the Tablets

To determine the release kinetics of the various systems studied, a revolving-basket dissolution apparatus (Dissolutest®, Sotax, Switzerland) equipped with 7 vessels whose dissolution media (500 ml) are thermostated at 37° C. is used. This apparatus, connected to a UVIKON 922 (Italy) spectrophotometer, is able to automatically carry out the sampling and the measurement of UV absorbance of the solutions contained in the various vessels. One of the vessels contains a solution of a known concentration in the active principle whose absorbance measured throughout the experiment constitutes the reference from which is calculated the percentage of the active principle dissolved in the vessel containing the solution studied.

The dissolution medium selected is a pH 6.8 buffer. The automatic sampling of the medium during the kinetics is carried out in the following way:

a sampling every 5 minutes during the first hour;
a sampling every 15 minutes until the appearance of a plateau for 100% of the dissolved active principle.

So as to increase the sensitivity of the dosage since the tablets are of a low dose, each dissolution vessel contains 3 tablets. In addition, the dissolution kinetics are carried out on 3 vessels. Table 3 summarizes the parameters used to carry out the dosage and the kinetics of the studied system.

The results of these measurements are presented in FIG. 1.

It is noted that the release of the active principle is much extended, since 100% is released only at the end of approximately 16 hours.

The qualitative and quantitative composition of the various excipients of the tablets obtained according to example 1 are summarized in table 6.

The characteristics of these tablets are summarized in table 7.

TABLE 3

Analytical methods and operating conditions used to characterize the assembled microgranules (bulk) and the ketoprofen-based tablets.

|  | Dosage (for uniformity of content) | | Dissolution | |
| --- | --- | --- | --- | --- |
|  | Bulk | Tablets | Bulk | Tablets |
| Number of units analyzed | 3 | 3 | 3 | 3 × 3 |
| Methods | UV detection at 257 nm (1) dissolution in a methanol/water mixture (3/1) | | Continuous UV at 260 nm (2) 500 ml pH 6.8 paddles 100 rpm | Continuous UV at 260 nm (2) 500 ml pH 6.8 baskets 50 rpm |
| Apparatus | UVIKON 922 (Italy) spectrophotometer | | SOTAX (Swiss) Dissolutest UVIKON 922 (Italy) spectrophotometer | |

(1) The choice of the wavelength was determined after establishment, of the spectrum of Ketoprofen in a methanol/water mixture (3/1).
(2) The choice of the wavelength was determined after establishment of the spectrum of Ketoprofen in the pH 6.8 dissolution medium.

Example 2

Ketoprofen Tablets with a 6% Xanthan Gum Base (Batch B5)

In this example, the method is exactly as in example 1, except that the quantity of xanthan gum used for the constitution of the polymeric layer of the microgranules is 6% by weight compared to the weight of the neutral support involved.

The qualitative and quantitative compositions of the various excipients of the tablets obtained according to example 2 are summarized in table 6.

The characteristics of these tablets are summarized in table 7.

Figure 2:
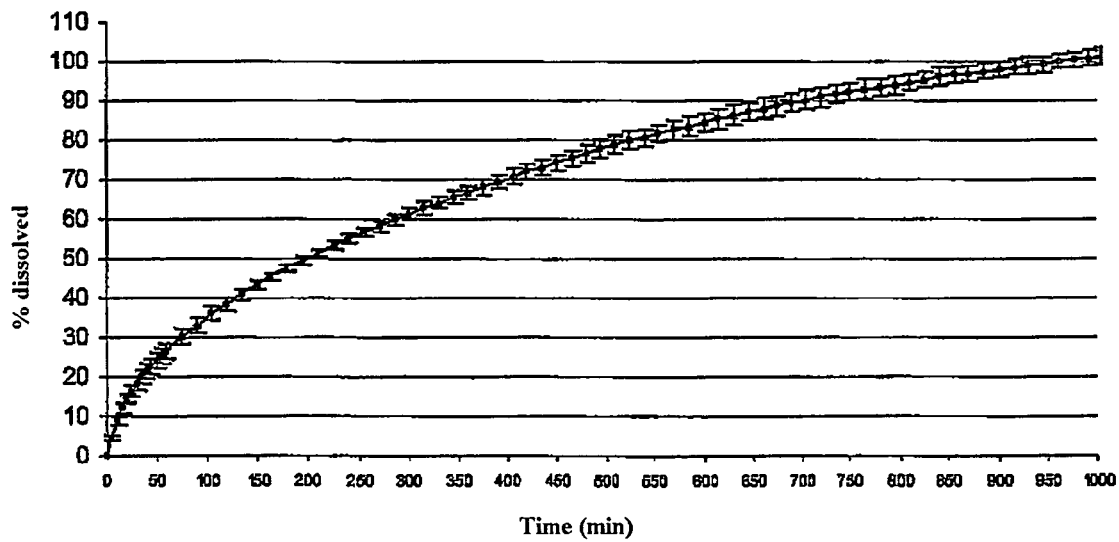
FIG. 2 represents the release profile of ketoprofen, used as the model active principle, obtained from tablets in conformity with the invention, obtained according to the method of example 2, whose polymeric layer comprises 6% by weight of xanthan gum (Rhodigel® 200 grade) compared to the weight of the neutral support.

The release kinetics of ketoprofen are determined under the same conditions as those of example 1. The results of these measurements are presented in FIG. 2.

Example 3

Tablets of the Active Principle (Ref.: 23015) with a 15% Xanthan Gum Base (Batch B10)

In this example, the method is exactly as in example 1, except that the quantity of xanthan gum used for the constitution of the polymeric layer of the microgranules is 15% by weight compared to the weight of the neutral support involved and that the principle involved is no longer ketoprofen but an active principle referred to as number 23015.

The qualitative and quantitative compositions of the various excipients of the tablets obtained after compression according to example 3 are summarized in the following table 4:

TABLE 4

Qualitative and quantitative compositions of the tablets of microgranules containing active principle 23015 obtained with 15% xanthan gum by weight compared to the weight of the neutral supports involved, which is 11.65% of the total weight of microgranules. (Batch B10)

| Type | Chemical name | Brand name | Quantity (g) (dry matter) |
| --- | --- | --- | --- |
| Support | Sugar sphere | Neutral 400-500 | 77.664 |
| Active | 23015 | not applicable | 1.230 |
| Matrix polymer | Xanthan gum | Rhodigel 200 | 11.651 |
| Binder | Povidone | PVP K30 | 3.160 |
|  | PEG 6000 | Renex PEG 6000 | 6.160 |
| Tensioactive | Polysorbate 80 | Polysorbate 80 | 0.010 |
| Lubricant | Magnesium stearate | not known | 0.125 |
| TOTAL |  |  | 100.000 |

Dissolution

The tablets thus obtained were then subjected to a dissolution test in 900 ml of pH 6.8 medium (in a 1 l flask: 6.805 g of $KH_2PO_4$, 22.4 ml of 1 N NaOH and 900 ml of purified water; adjusted if necessary to pH 6.8 with soda then brought up to 1 l with water).

Each tablet is placed in a basket, turning at 50 rpm.

Then, at 1, 4, 8, 12, 16, 20 and 24 hours, the dissolution medium is sampled and the sample is assayed by HPLC (high-performance liquid chromatography) with UV detection.

The results obtained for 3 dissolution vessels are summarized in the following table 5:

TABLE 5

Dissolution profile of the tablets of microgranules of active principle 23015 powdered with 15% xanthan gum.

|  | Time [h] | | | | | | | |
| --- | --- | --- | --- | --- | --- | --- | --- | --- |
|  | 0 | 1 | 4 | 8 | 12 | 16 | 20 | 24 |
| Average [%] | 0 | 13.7 | 38.7 | 65.3 | 83.5 | 94.1 | 98.9 | 100.6 |
| Variation Coefficient [%] | 0 | 5.2 | 0.9 | 1.3 | 0.5 | 0.7 | 1.3 | 0.9 |

In this example, the tablets of the microgranules in conformity with the invention, exhibit a $T_{50}$ equal to 340 min, which is 5 h 40 min, and a T80 equal to 675 min, which is 11 h 15 min.

Figure 10:
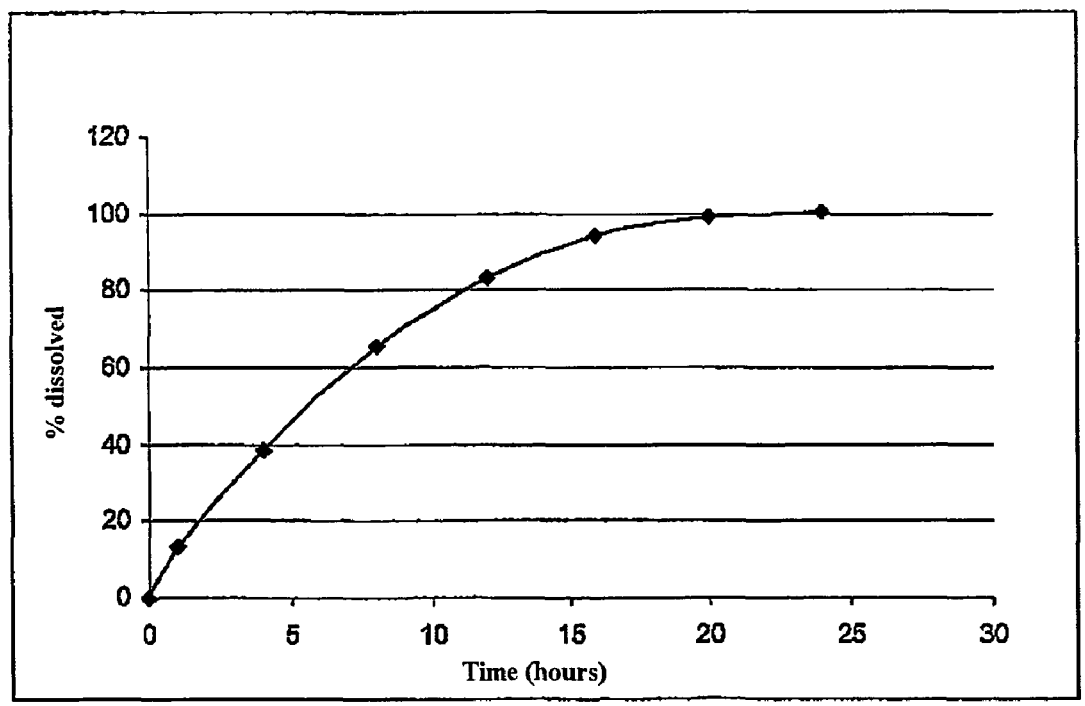
FIG. 10 represents the release profile of the active principle 23015, obtained from the tablets in conformity with the invention, obtained according to the method of example 3, whose polymeric layer comprises 15% by weight of xanthan gum (Rhodigel® 200 grade) compared to the weight of the neutral support.

These results are represented on FIG. 10.

Example 4

Tablets of Microgranules of Ketoprofen Containing 5% of 100,000 mPa·s HPMC (Batch B6)

a) Application of HPMC by Powdering

As in example 1, a mass of 2 kg of neutrals of 400 µm to 500 µm (Suglets®) is set in rotation in a conventional coating pan.

Then a moistening step similar to that described in example 1 is carried out from an aqueous binding solution of 15% PVP K30 (169 grams of binding solution including 25 grams of PVP).

The polymer of interest is a hydrophilic polymer with gelling properties: HPMC sold under the brand name Metolose® 90 HS, whose viscosity is 100,000 mPa·s. (millipascal second) for a 2% w/w aqueous solution at 20° C.

100 grams of HPMC (which is 5% by weight compared to the weight of the neutrals involved) are introduced manually in the coating pan in rotation. As described in example 1, a drying phase follows the powdering sequence.

b) Application of Ketoprofen by Spraying

The active principle used is ketoprofen at 0.4% by weight compared to the weight of the neutrals involved, which is 8 grams. The active layer is applied in an air fluidized bed (AFB) as in example 1, from a solution containing, in the dissolved state, the active principle and the binding agent (5% $PEG_{6000}$ by weight compared to the weight of the neutrals) in pH 8 buffer (2000 grams).

c) Drying and Screening

A drying phase and a screening phase identical to those of example 1 are carried out on the mass of microgranules before compression.

d) Compression

Before compression, the assembled neutrals are lubricated with 0.125% w/w magnesium stearate (MgSt). The mixing is carried out in a Turbula® mixer for 2 min at 48 rpm. The mixture is then compressed on a Frogerais OA alternative press by applying a compression force of 250 MPa.

e) Dosage and Dissolution of the Tablets

As in example 1, the tablets obtained are dissolved in a Dissolutest® and the quantity of the active principle released in the medium is measured as a function of time.

Figure 3:
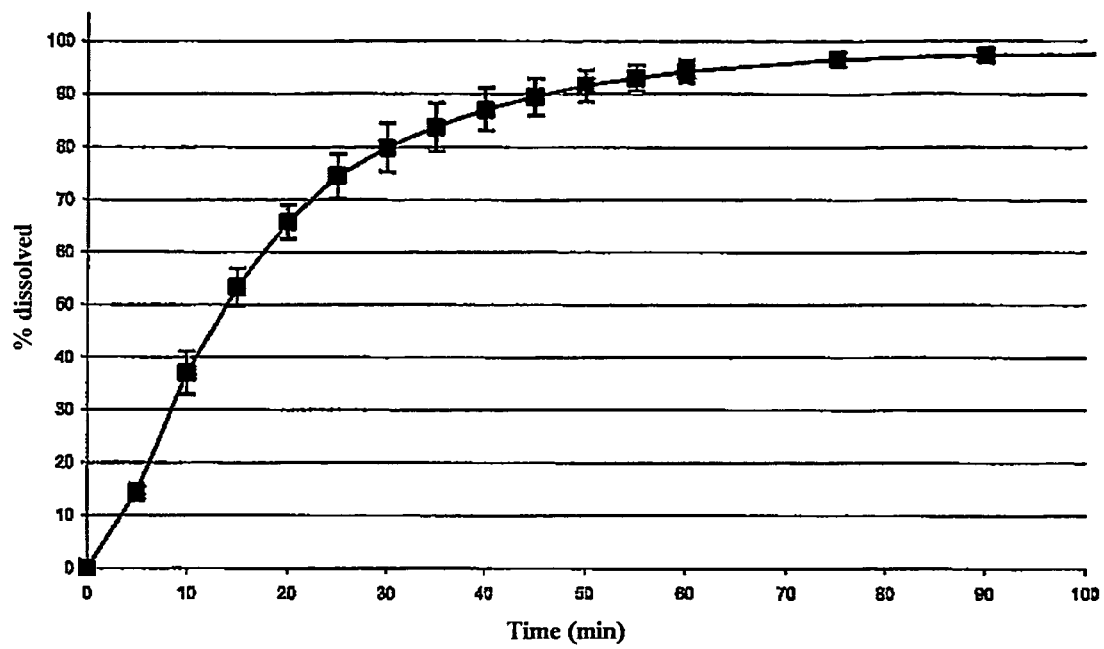
FIG. 3 represents the release profile of ketoprofen, used as the model active principle, obtained from tablets in conformity with the invention, obtained according to the method of example 4, whose polymeric layer comprises 5% by weight of HPMC of viscosity 100,000 mPa·s in a 2% w/w aqueous solution at 20° C. (Metolose® 90 SH grade) compared to the weight of the neutral support.
Figure 4:
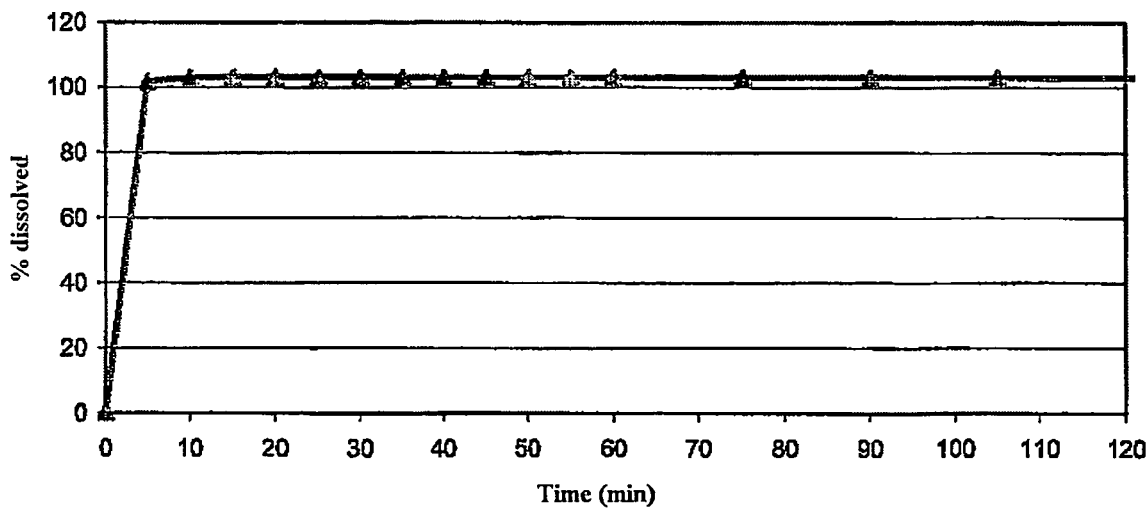
FIG. 4 represents the release profile of ketoprofen obtained from "bulk," that is, not compressed, ketoprofen microgranules comprising 2% by weight of xanthan gum (Rhodigel® 200 grade) compared to the weight of the neutral support. These microgranules are obtained in accordance with the method described in example 1, but without the compression step d).
Figure 5:
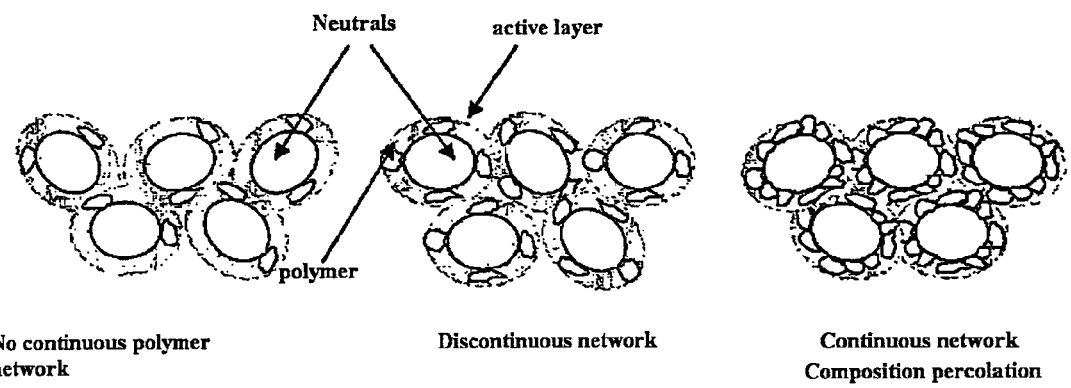
FIG. 5 is the schematic representation of the formation of the polymeric network of the tablets according to the present invention. More particularly.
Figure 6:
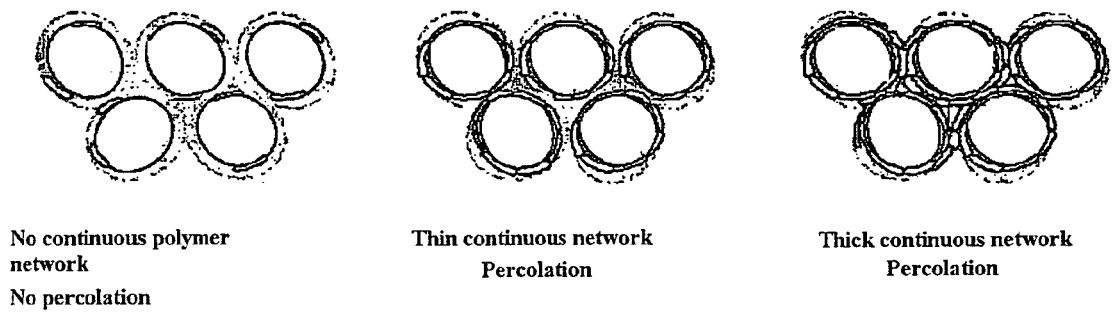
FIG. 6 is the electronic microscopy photograph of the functionalized excipients in conformity with the invention after the step of the powdering of the polymer.

The results of these measurements are presented in FIG. 3.

It is noted that the release profile of the active principle is also much extended, since only 80% of the active principle is released after 30 minutes as is represented in FIG. 3.

B) Qualitative and Quantitative Compositions of the Various Excipients of the Tablets Obtained According to Example 4, and Their Dissolution Characteristics.

TABLE 6

Composition of a batch containing hydroxypropylmethylcellulose (HPMC) (all percentages are of the weight of the product compared to the weight of the neutrals involved, which is 2000 g).

| | | Phase 1: Powdering | | | Quantity | Phase 2: AFB | |
|---|---|---|---|---|---|---|---|
| Example | Batch number | Quantity of polymer | Quantity of binding solution | Quantity of PVP (15% of the solution) | Quantity of active principle | Quantity of PEG | Quantity of solvent |
| 4 | B6 | 5% HPMC (100 g) | 169 g | 25 g | 0.4% | 5% | 2000 g |

TABLE 7

Measurements of certain characteristics of the tablets obtained according to example 4.

| | B6 |
|---|---|
| Overall weight yield (%) | 95.8 |
| Mean tablet weight (mg) (n = 20) | 506.3 ± 7.1 |
| Theoretical starting titer (mg/cp) | 1.77 |

TABLE 7-continued

Measurements of certain characteristics of the tablets obtained according to example 4.

| | B6 |
|---|---|
| Real Titer obtained (mg/cp) | 1.74 ± 0.02 |
| $T_{50}$ (minutes) (*) | 14 |
| $T_{80}$ (minutes) (*) | 30 |

(*) $T_{50}$ and $T_{80}$ correspond to the time at which 50% and 80%, respectively, of the active principle is dissolved in the dissolution medium.

Example 5

Comparison of the Dissolution Profiles of the Tablets of Microgranules of Ketoprofen Containing 5%, 10% and 15% of 100,000 mPa·s HPMC (Batches B7, B8, and B9)

In this example, the applicant compared the in vitro dissolution kinetics of the tablets of microgranules of ketoprofen obtained according to the method described in example 4 but from starting neutral cores of a diameter between 250 μm and 355 μm respectively powdered with 5%, 10% and 15% of Metolose® 90SH HPMC (Shin Etsu, Japan, Batch 0203021) whose viscosity is 100,000 mPa·s for a 2% w/w aqueous solution at 20° C. These tablets are obtained after having been subjected to a compression stress of 250 MPa.

As in example 1, the tablets obtained are dissolved in a Dissolutest® and the quantity of the active principle released in the medium is measured as a function of time.

Determination of the Influence of Polymer Concentration

Figure 7:
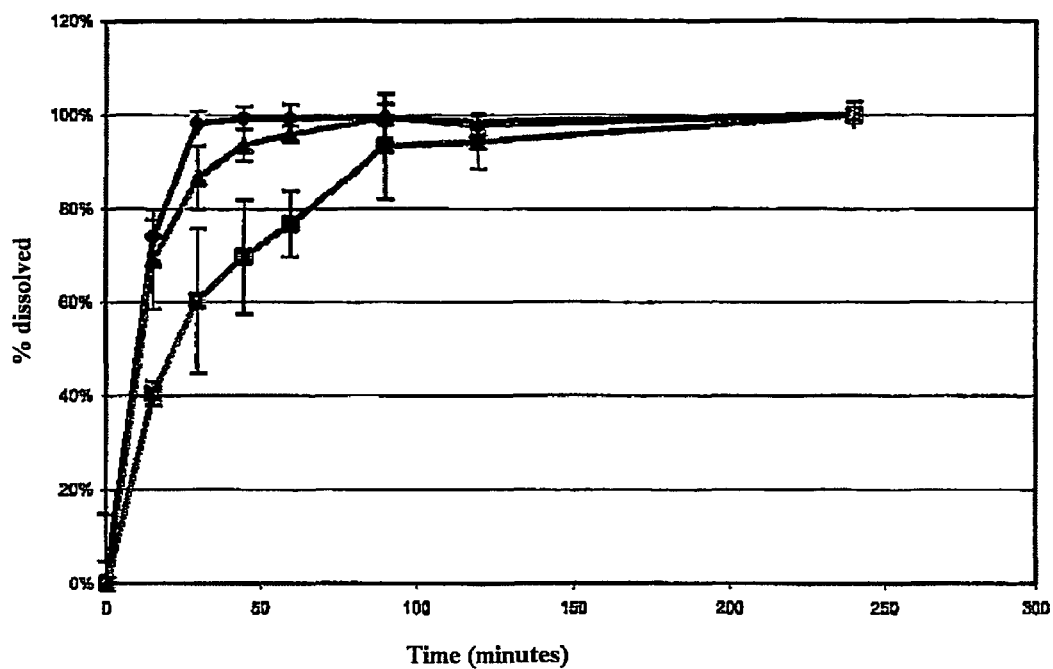
FIG. 7 represents the release profile of ketoprofen, obtained from tablets in conformity with the invention, obtained according to the method of example 5, whose polymeric layer comprises respectively 5%, 10% and 15% by weight of HPMC compared to the weight of the neutral support.
- ◆- Batch B7 (5% of HPMC)-250 MPa
- ▲- Batch B8 (10% of HPMC)-250 MPa
- ■- Batch B9 (15% of HPMC)-250 MPa

FIG. 7 represents the release kinetics of the tablets from batches B7, B8 and B9.

Table 8 also compares the $T_{50}$ and $T_{80}$ measured for each batch.

$T_{50}$=time at which 50% of the active principle is released.

$T_{80}$=time at which 80% of the active principle is released.

FIG. 7 shows that the dissolution kinetics of batches B7 and B8 are rather similar and of a slightly extended type, since 85% to 95% of the active principle is released after 30 minutes.

On the other hand, the release kinetics of batch B9 is much slowed compared to the other two batches: the $T_{50}$ of batch B9 is up to two times higher than that of the $T_{50}$ of batches B7 and B8 (table 8).

Thus, the applicant has demonstrated that the quantity of 100,000 mPa·s HPMC only truly influences the release kinetics beyond a certain threshold of between 10% and 15% w/w of this polymer. Beyond this threshold, the release kinetics of the active principle are much slowed and a true extended-release profile is observed. In addition, the applicant has noted that this threshold varies as a function of the size of the starting neutral cores.

Indeed, it is only above this range of concentrations that the polymer layer is dense enough to form a true network responsible for the release of the active principle according to a truly extended profile.

TABLE 8

Estimate of the times of the release of 50% and 80% of the active principle for the 3 batches studied.

| Batch | $T_{50}$ (min) | $T_{80}$ (min) |
|---|---|---|
| B7 | 10.1 | 24.4 |
| B8 | 10.9 | 26.5 |
| B9 | 24.9 | 77.2 |

Example 6

Tablets of Microgranules of Ketoprofen Containing 2%, 5% and 10% of Carbopol® 971 P (Batches C1, C2, and C3)

In this example, the applicant measured the dissolution profiles of ketoprofen from the tablets of microgranules obtained by the powdering according to the method described in example 5 of a synthetic polymer of the family of carbomers: Carbopol® 971 P (Noveon, USA, batch 0308024) which can be used in formulations for extended-release tablets.

The batches C1, C2 and C3 represent tablets of microgranules powdered with 2%, 5% and 10%, respectively, of this carbomer and compressed at 150 MPa.

The neutrals applied with the polymeric layer of Carbopol® 971 P are then subjected to the ketoprofen application step. As in example 1, this step is carried out in a Hüttlin (Germany) Kugelcoater® air fluidized bed (AFB).

Figure 8:
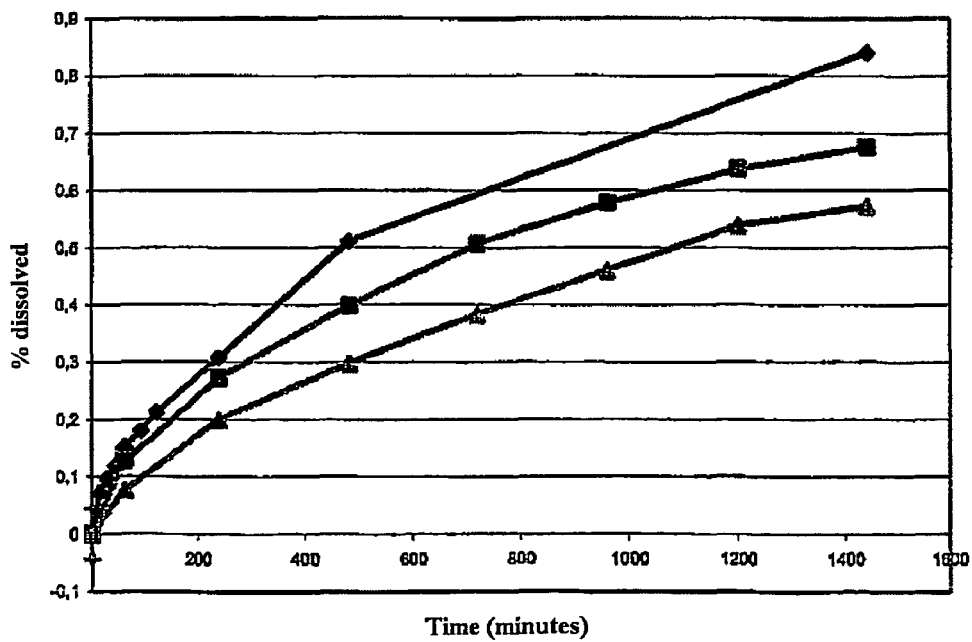
FIG. 8 represents the release profile of ketoprofen, obtained from tablets in conformity with the invention, obtained according to the method of example 6, whose polymeric layer comprises respectively 2%, 5% and 10% by weight of Carbopol® 971 P compared to the weight of the neutral supports. These kinetics are obtained by sampling from the dissolution medium and assaying the samples by HPLC (high-performance liquid chromatography) then by UV detection.
- ◆- Batch C1: 2% of Carbopol®
- ▲- Batch C2: 5% of Carbopol®
- ■- Batch C3: 10% of Carbopol®

FIG. 8 represents the release kinetics of the tablets from the batches C1 to C3 of which the quantity in Carbopol® varies from 2% to 10%. These kinetics are obtained by the sampling of the dissolution medium and the dosage of the samples by HPLC (high-performance liquid chromatography) then UV detection. This figure shows that the release kinetics of the active principle slow as the quantity of Carbopol® increases.

Indeed, the $T_{50}$ of batch C1 is 8 h whereas the $T_{50}$ of batch C3 (which contains five times more polymer than batch C1) is approximately 18 h (see table 9).

This example shows that the use of this polymer makes it possible to observe much-extended release kinetics: the $T_{80}$ of the three batches are all greater than 20 h, and this without the beginnings of a plateau.

Figure 9:
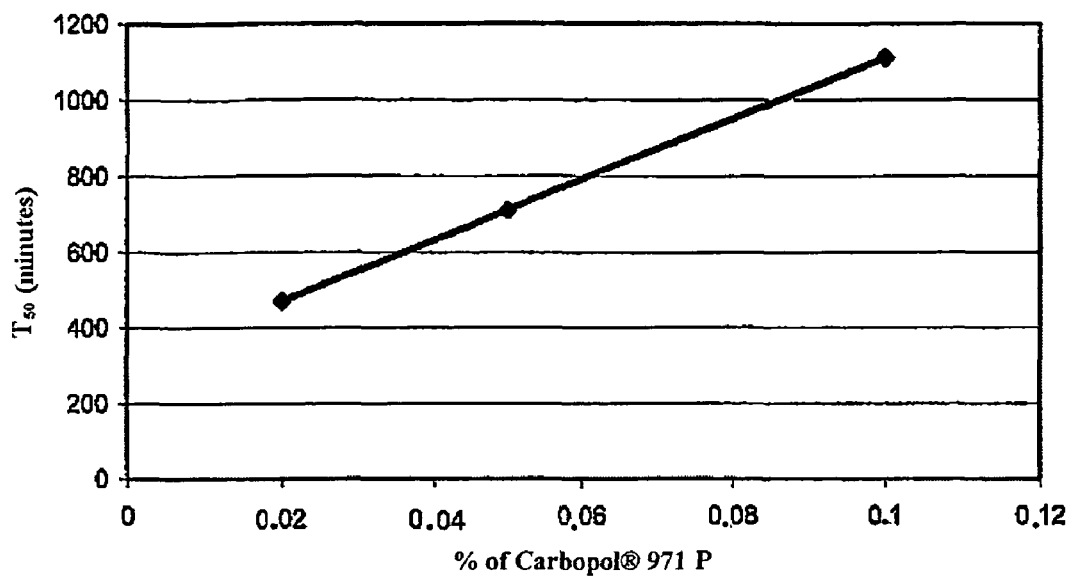
FIG. 9 represents the variation of $T_{50}$ as a function of Carbopol® 971 P for the tablets according to example 6.

In addition, the applicant has demonstrated that, as is shown in FIG. 9 for this polymer, there is a linear variation of $T_{50}$ as a function of the quantity of the polymer used.

This property is particularly advantageous insofar as it can be used in order to know the $T_{50}$ of a given percentage of Carbopol® or, conversely, to evaluate what percentage of Carbopol® must be used to obtain a given $T_{50}$.

TABLE 9

Estimate of the times of release of 50% and 80% of the active principle for the 3 batches powdered with Carbopol ® 971P studied.

| Batch | $T_{50}$ (hours) | $T_{80}$ (hours) |
|---|---|---|
| C1 | 8 | 22 |
| C2 | 12 | More than 24 hours |
| C3 | 18 | More than 24 hours |

Example 7

Tablets of Microgranules Containing 0.5% and 1% of Disintegrating Agents (Batches D1, D2 and D3)

In this example, the applicant endeavored to demonstrate the disintegrating character of the tablets of microgranules obtained in accordance with the method described in example 5, except that no active principle is bound on the previously-powdered granules: the step of the application by spraying in the AFB is not carried out in this example.

The details of the composition of the various batches are presented in table 10.

The powdering is carried out as described in the preceding examples with 3 types of excipients with disintegrating properties: branched polyvinylpyrrolidone (batch D1), sodium carboxymethyl starch (batch D2) and croscarmellose sodium (batch D3).

For this purpose, for each type of disintegrant 2 sub-batches, each comprised of the tablets of powdered microgranules at 0.5% (batches D1, D2 and D3) and at 1% (batches D1', D2' and D3') of the disintegrating polymer, were tested.

A disintegration test was carried out under the conditions recommended by the European Pharmacopeia. In such a test, the tablets are placed in hollow cylindrical tubes at the bottom of which is a metal screen of a 2 mm mesh that retains the tablet inserted in each tube. The entire apparatus is submerged in a water bath. The tubes are then subjected to a regular, alternating vertical movement of approximately 30 cycles per minute.

The total disintegration time of the tablet is measured when no residue of the tablet remains on the surface of the screen.

For each of these batches the time of disintegration of the last disaggregated tablet was determined on a total of 6 tablets by sub-batches.

In addition, for each sub-batch the applicant tested 2 different compression force values, expressed in table 11 in the form of the result in terms of cohesion acquired, that is, a rupturing stress of approximately 0.3 MPa and a rupturing stress of approximately 0.5 MPa.

Batches D1 and D1': the branched polyvinylpyrrolidone used respectively at 0.5 and 1% for the constitution of batch D1 is sold under the brand name Polyplasdone® XL10 (ISP, Switzerland, batch 0404046), which is a disintegrant that is insoluble in water and is generally used at concentrations from 2% to 5% in tablets prepared by wet granulation, dry granulation or direct compression.

This polymer is characterized by a large hydration capacity but with a low tendency to form a gel.

Batches D2 and D2': in this example, with a concern for a comparison with the other disintegrants tested, the applicant used the sodium carboxymethyl starch Explosol® (Blanver, Brazil, 0311044) at 0.5% and 1% w/w for the constitution of the tablets of microgranules of batches D2 and D2'.

Low-substituted sodium carboxymethyl starches and sodium starch glycolate are low-substituted and branched starch derivatives which can be used in direct compression or after wet granulation.

Batches D3 and D3': the croscarmellose sodium used in this example at 0.5 and 1%, respectively, for batches D3 and D3' is Vivasol® (Pirna, Germany, Lot 0404041), or branched sodium carboxymethylcellulose. It is an excipient classically used in oral dosage forms as a disintegrant in tablets or granules.

TABLE 10

Definition and composition of the batches as a
function of the quality and the quantity of the polymer used.

| Batch | Batch name | Quantity of polymer |
|---|---|---|
| XNPT 4610 | D1 | 0.5% of branched polyvinylpyrrolidone (10 g) |
| XNPT 4579 | D1' | 1% of branched polyvinylpyrrolidone (20 g) |
| XNPT 4580 | D2 | 0.5% of sodium carboxymethyl starch (10 g) |
| XNPT 4581 | D2' | 1% of sodium carboxymethyl starch (20 g) |
| XNPT 4582 | D3 | 0.5% of croscarmellose sodium (10 g) |
| XNPT 4609 | D3' | 1% of croscarmellose sodium (20 g) |

TABLE 11

Disintegration times of the tablets of the batches
of tablets of microgranules containing a disintegrating agent
for two rupturing stress values.

| | | Rupturing stress of approximately 0.3 MPa | Rupturing stress of approximately 0.5 MPa |
|---|---|---|---|
| 0.5% branched polyvinylpyrrolidone | D1 | 19 seconds | 1 minute |
| 1% branched polyvinylpyrrolidone | D1' | 26 seconds | 2 minutes 13 seconds |
| 0.5% sodium carboxymethyl starch | D2 | 21 seconds | 1 minute and 46 seconds |
| 1% sodium carboxymethyl starch | D2' | 32 seconds | 2 minutes and 8 seconds |
| 0.5% croscarmellose sodium | D3 | 34 seconds | 3 minutes and 5 seconds |
| 1% croscarmellose sodium | D3' | 27 seconds | 1 minute and 45 seconds |

This example shows first of all that the disintegrant-based tablets obtained according to the characteristics of the present invention well exhibit a capacity to disaggregate quickly (in less than 3 minutes) in an aqueous medium, and this for very small quantities of the polymer.

In addition, this example shows the influence of compression force on the disintegration rate of these tablets. Thus, quite logically, the lower the force of compression (and of rupture), the more rapidly the tablets obtained disaggregate. Indeed, the less the powdered microgranules are compressed, the wider the porous network will be, and the more easily will the liquid medium pass through, thus favoring the rapid disintegration of the structure.

On the other hand, this example shows that the influence of the nature of the disintegrating polymer used on the disintegration time of the tablets is minimal, even none.

The invention claimed is:

1. Tablets obtained by the direct compression of microgranules which are comprised of:
   a neutral support,
   said neutral support being coated with a polymeric layer comprising at least one pharmaceutically acceptable polymer,
   said polymeric layer being coated with an active layer containing at least one active principle,
   wherein the active principle is located in the active layer but is not in the polymeric layer and the polymeric layer is present between the neutral support and the active layer, and the amount of said at least one active principle is less than 50 mg per tablet.

2. The tablets according to claim 1, wherein said polymeric layer contains in addition at least one pharmaceutically acceptable binding agent.

3. The tablets according to the claim 1, wherein the total quantity of the polymer of said polymeric layer represents between 1% and 100% by weight of the weight of the neutral support.

4. The tablets according to claim 1, wherein said polymer is selected among the extended-release polymers and the disintegrating polymers.

5. The tablets according to claim 4, wherein said disintegrating polymers are selected from the group consisting of polyvinylpyrrolidone derivatives, starch derivatives, calcium and magnesium salts, alginates and cellulose derivatives, as well as mixtures thereof.

6. The tablets according to claim 5, wherein said disintegrating polymers are selected from the group consisting of crospovidone, povidone, sodium carboxymethylcellulose, croscarmellose sodium, methylcellulose, low-substituted hydroxypropylcellulose, sodium carboxymethyl starch and branched starch, as well as mixtures thereof.

7. The tablets according to claim 4, wherein said extended-release polymers are selected among hydrophilic polymers with gelling properties.

8. The tablets according to claim 7, wherein said extended-release polymers are selected from the group consisting of polymers derived from cellulose, natural or modified natural polysaccharides, galactomannans, glucomannans, succinoglycans, scleroglucans, carbomers and poly(ethylene oxides), as well as mixtures thereof.

9. The tablets according to claim 8, wherein said polymers derived from cellulose are cellulose ethers of medium to high viscosity selected from the group consisting of hydroxyethylcellulose, hydroxypropylcellulose, and hydroxypropylmethylcellulose, as well as mixtures thereof.

10. The tablets according to claim 8, wherein said gums are selected from the group consisting of alginic acid, alginates, agar-agar, carrageenans, carob gum, gum guar, gum tragacanth, gum arabic, cassia gum, xanthan gum, gum karaya, tara gum and gellan gum, as well as mixtures thereof.

11. The tablets according to claim 4, wherein said extended-release polymers are selected from the group consisting of polymers and copolymers derived from methacrylic acid insoluble in water regardless of pH, as well as mixtures thereof.

12. The tablets according to claim 11, wherein said extended-release polymers are selected among poly(ethyl acrylate, methyl methacrylate, trimethylamonioethyl methacrylate) chlorides.

13. The tablets according to claim 4, wherein said extended-release polymers are selected among cellulose derivatives insoluble in water, as well as mixtures thereof.

14. The tablets according to claim 13, wherein said extended-release polymers are selected from the group consisting of ethylcellulose and cellulose acetate, as well as mixtures thereof.

15. The tablets according to claim 4, wherein said extended-release polymers are selected from the group consisting of mucoadhesive polymers, carbomers, sodium alginate, hydroxyethylcellulose, hydroxypropyl-cellulose, hydroxypropylmethylcellulose, gelatin, guar gum, poly(ethylene oxide), dextrin and chitosan.

16. The tablets according to claim 1, wherein said polymeric layer comprises in addition a wax or a derivative thereof, a glycerol fatty acid derivative, or a mixture thereof.

17. The tablets according to claim 16, wherein the wax is selected among natural beeswax and purified beeswax.

18. The tablets according to claim 16, wherein the glycerol fatty acid derivative is selected from the group consisting of glycerol monostearate, glycerol monooleate, glycerol palmitostearate, and mixtures of the fatty acid esters and glycerides of polyethylene glycol.

19. The tablets according to claim 1, wherein said active layer contains in addition at least one pharmaceutically acceptable binding agent.

20. The tablets according to claim 1, wherein said neutral support is a microsphere comprised of sucrose and of corn starch, of a size between 50 µm and 3000 µm.

21. The tablets according to claim 1, wherein they contain in addition a lubricant in a quantity less than 5% by weight compared to the total weight of the tablet.

22. The tablets according to claim 1, wherein in addition they are coated by one or more layers of film-coating agents.

23. The tablets according to claim 22, wherein said film-coating agents are gastroresistant film-coating agents selected from the group consisting of polymers derived from methacrylic acid, from derivatives of polyvinyl acetate, from ethyl acrylate and from derivatives of cellulose, as well as mixtures thereof.

24. The tablets according to claim 1, wherein the at least one active principle is selected from the group consisting of hormones and derivatives thereof, active principles acting on the central nervous system, active principles acting on the cardiovascular system, antibiotics, antivirals, analgesics and anti-inflammatories.

25. The tablets according to claim 24, wherein said active principles acting on the central nervous system are selected from the group consisting of anti-epileptics, anti-Parkinson's drugs, psychostimulants, psychotropics, antidepressants, anxiolytics and antipsychotics.

26. The tablets according to claim 24, wherein said active principles acting on the cardiovascular system are selected from the group consisting of antihypertensives, antithrombotics, anti-aggregating agents and cholesterol-lowering agents.

27. The tablets according to claim 1, wherein the at least one active principle is distributed homogeneously.

28. The tablets according to claim 1, provided in scored form.

29. A method of preparation of the tablets according to claim 1, comprising the following steps:
moistening the neutral support beforehand using a dampening solution optionally containing a binding agent;
then applying the polymer to the surface of the neutral support by powdering to form a polymeric layer;
spraying a layering solution comprising the at least one active principle and optionally a binding agent on the surface of the polymeric layer;
drying and then directly compressing the microgranules thus obtained;
optionally coating the tablets thus obtained with one or more layers of a film-coating agent.

30. The method of preparation of the tablets according to claim 1, wherein the compressing is carried out using a lubricant at less than 5% by weight compared to the total weight of the tablets.

31. A method for administering a low dose of active principle to a patient comprising orally administering to said patient a low dose tablet according to claim 1.

32. The method according to claim 31, comprising sublingually or transmucosally administering said tablet to said patient.

33. The tablets according to claim 3, wherein the total quantity of polymer of said polymeric layer represents between 1% and 50% by weight of the weight of the neutral support.

34. The tablets according to claim 7, wherein the total quantity of polymer of said hydrophilic polymers has a viscosity higher than 1000 mPa·s, measured in a 2% w/w aqueous solution at 20° C.

35. The tablets according to claim 8, wherein said natural or modified natural polysaccharides are gums.

36. The tablets according to claim 15, wherein the mucoadhesive polymer is sodium carboxymethylcellulose.

37. The tablets according to claim 18, wherein said mixtures of the fatty acid esters and glycerides of polyethylene glycol are those belonging to the lauroyl macrogolglycerides family.

38. The tablets according to claim 20, wherein said neutral support is of a size between 100 µm and 1000 µm.

39. The tablets according to claim 20, wherein said neutral support is of a size between 100 µm and 500 µm.

40. The tablets according to claim 23, wherein said polymers derived from methacrylic acid are copolymers of methacrylic acid.

41. The tablets according to claim 23, wherein said derivatives of polyvinyl acetate are polyvinyl acetate phthalate and polymethacrylic acid.

42. The tablets according to claim 23, wherein said derivative of cellulose is hydroxypropylmethyl cellulose phthalate.

43. The tablets according to claim 1, wherein said tablets contain less than 25 mg of the active principle.

44. The tablets according to claim 1, wherein said tablets contain less than 10 mg of the active principle.

45. The method according to claim 31, wherein the release of at least one active principle must be modified over time.

* * * * *